(12) United States Patent
Newman et al.

(10) Patent No.: US 11,963,880 B2
(45) Date of Patent: Apr. 23, 2024

(54) CANNULATED BONE IMPLANT

(71) Applicant: GENSANO LLC, Reno, NV (US)

(72) Inventors: Brian M. Newman, Reno, NV (US);
William R. Adams, Paducah, KY (US);
Michael J. Joyer, Reno, NV (US)

(73) Assignee: GENSANO LLC, Reno, NV (US)

( * ) Notice: Subject to any disclaimer, the term of this patent is extended or adjusted under 35 U.S.C. 154(b) by 0 days.

(21) Appl. No.: 18/053,883

(22) Filed: Nov. 9, 2022

(65) Prior Publication Data

US 2023/0065701 A1 Mar. 2, 2023

Related U.S. Application Data

(63) Continuation of application No. PCT/US2021/031633, filed on May 10, 2021.
(Continued)

(51) Int. Cl.
*A61F 2/42* (2006.01)
*A61F 2/30* (2006.01)

(52) U.S. Cl.
CPC ........ *A61F 2/4225* (2013.01); *A61F 2/30749* (2013.01); *A61F 2/30771* (2013.01);
(Continued)

(58) Field of Classification Search
CPC ........ A61F 2/4225; A61F 2/4241; A61F 2/42; A61B 17/7291; A61B 17/864; A61B 2017/565; A61B 17/7052; A61B 17/748
See application file for complete search history.

(56) References Cited

U.S. PATENT DOCUMENTS 5,207,712 A 5/1993 Cohen
7,041,106 B1 5/2006 Carver et al.
(Continued)

FOREIGN PATENT DOCUMENTS

AU 2006234593 10/2006
AU 2014203105 3/2015
(Continued)

OTHER PUBLICATIONS

Cannulink Intraosseous Fixation System, Wright Medical Group, Wright.com, in 2 pages, believed to be available to the public prior to May 11, 2020.
(Continued)

*Primary Examiner* — Marcia L Watkins
(74) *Attorney, Agent, or Firm* — Knobbe, Martens, Olson & Bear, LLP

(57) ABSTRACT

Various cannulated bone implants and methods of using the cannulated bone implant are disclosed. The cannulated bone implant can include a proximal portion, a proximal end, a distal portion, a distal end, a transition portion, a threaded portion, a finned portion and a central passage. The transition portion can comprise a bend positioned between the proximal portion and the distal portion. The threaded portion can be positioned along the proximal portion between the proximal end and the transition portion. The threaded portion can be configured to secure the implant into a bone of a patient. The finned portion can be positioned along the distal portion between the transition portion and the distal end. The finned portion can be configured to prevent migration and/or rotation of the implant in use. The central passage can extend linearly from the proximal end of the implant to the distal end of the implant.

20 Claims, 7 Drawing Sheets

Related U.S. Application Data

(60) Provisional application No. 63/023,139, filed on May 11, 2020.

(52) U.S. Cl.
CPC ............ *A61F 2002/30326* (2013.01); *A61F 2002/30593* (2013.01); *A61F 2002/30622* (2013.01); *A61F 2002/30866* (2013.01); *A61F 2002/4228* (2013.01)

(56) References Cited

U.S. PATENT DOCUMENTS

| | | | |
|---|---|---|---|
| 9,138,274 | B1 | 9/2015 | Biesinger et al. |
| 9,750,553 | B1 | 9/2017 | Forrester et al. |
| 10,470,890 | B2 | 11/2019 | Austin et al. |
| 2005/0283159 | A1 | 12/2005 | Amara |
| 2006/0036251 | A1 | 2/2006 | Reiley |
| 2008/0132958 | A1 | 6/2008 | Pech et al. |
| 2008/0195215 | A1 | 8/2008 | Morton |
| 2010/0121324 | A1 | 5/2010 | Tyber et al. |
| 2011/0082508 | A1 | 4/2011 | Reed |
| 2011/0257652 | A1 | 10/2011 | Roman |
| 2011/0301652 | A1 | 12/2011 | Reed et al. |
| 2011/0301653 | A1 | 12/2011 | Reed et al. |
| 2012/0065692 | A1 | 3/2012 | Champagne et al. |
| 2012/0089197 | A1 | 4/2012 | Anderson |
| 2012/0209337 | A1 | 8/2012 | Weinstein |
| 2013/0123862 | A1 | 5/2013 | Anderson et al. |
| 2013/0131822 | A1 | 5/2013 | Lewis et al. |
| 2013/0150965 | A1 | 6/2013 | Taylor et al. |
| 2013/0190830 | A1 | 7/2013 | Champagne et al. |
| 2013/0317559 | A1 | 11/2013 | Leavitt et al. |
| 2014/0052196 | A1 | 2/2014 | McGinley et al. |
| 2014/0107712 | A1 | 4/2014 | Fallin et al. |
| 2014/0114415 | A1 | 4/2014 | Tyber |
| 2014/0276825 | A1 | 9/2014 | Brown et al. |
| 2014/0276827 | A1 | 9/2014 | Roman et al. |
| 2014/0277186 | A1 | 9/2014 | Granberry et al. |
| 2014/0277554 | A1 | 9/2014 | Roman et al. |
| 2015/0012050 | A1 | 1/2015 | Anderson |
| 2015/0073412 | A1 | 3/2015 | Faux |
| 2015/0073413 | A1 | 3/2015 | Palmer et al. |
| 2015/0112341 | A1 | 4/2015 | Penzimer et al. |
| 2015/0142066 | A1 | 5/2015 | Shemwell et al. |
| 2015/0374503 | A1 | 12/2015 | Lovick et al. |
| 2016/0015437 | A1 | 1/2016 | Elleby et al. |
| 2016/0045324 | A1 | 2/2016 | Austin et al. |
| 2016/0081727 | A1 | 3/2016 | Munday et al. |
| 2016/0256290 | A1 | 9/2016 | Seavey et al. |
| 2016/0270923 | A1 | 9/2016 | Finley et al. |
| 2016/0354127 | A1 | 12/2016 | Lundquist et al. |
| 2017/0035474 | A1 | 2/2017 | McCormick et al. |
| 2017/0065424 | A1 | 3/2017 | Lauf et al. |
| 2017/0100171 | A1 | 4/2017 | Palmer et al. |
| 2017/0151061 | A1 | 6/2017 | Lavi |
| 2017/0156766 | A1 | 6/2017 | Anderson et al. |
| 2017/0189090 | A1 | 7/2017 | Champagne et al. |
| 2017/0273727 | A1 | 9/2017 | Roman et al. |
| 2017/0333081 | A1 | 11/2017 | Cordier et al. |
| 2017/0340370 | A1 | 11/2017 | Chen |
| 2018/0021145 | A1 | 1/2018 | Seavey et al. |
| 2018/0049881 | A1 | 2/2018 | Austin et al. |
| 2018/0055623 | A1 | 3/2018 | Blacklidge |
| 2018/0161170 | A1 | 6/2018 | Petrano |
| 2018/0168703 | A1 | 6/2018 | Roman et al. |
| 2018/0235765 | A1 | 8/2018 | Welker et al. |
| 2018/0243018 | A1 | 8/2018 | Lintula et al. |
| 2018/0303615 | A1 | 10/2018 | Papaloïzos |
| 2018/0317987 | A1 | 11/2018 | Champagne et al. |
| 2019/0070013 | A1* | 3/2019 | Champagne ....... A61B 17/7291 |

FOREIGN PATENT DOCUMENTS

| | | |
|---|---|---|
| BR | 102013032137 | 12/2015 |
| CA | 2283190 | 9/1998 |
| CA | 2521977 | 10/2004 |
| CA | 2753032 | 8/2010 |
| CA | 2791967 | 9/2011 |
| CA | 2811130 | 5/2012 |
| CA | 2816438 | 11/2013 |
| CA | 2874476 | 11/2013 |
| CA | 2836645 | 6/2014 |
| CA | 2836967 | 6/2014 |
| CA | 2837497 | 6/2014 |
| CA | 2837571 | 6/2014 |
| CA | 2864697 | 4/2015 |
| CA | 2896933 | 9/2015 |
| CA | 2887570 | 3/2016 |
| CA | 2889595 | 6/2016 |
| CA | 2896953 | 7/2016 |
| CN | 201253253 | 6/2009 |
| CN | 203885606 | 10/2014 |
| DE | 102015107056 | 11/2016 |
| DE | 102015013613 | 4/2017 |
| EP | 1493399 | 1/2005 |
| EP | 1927322 | 6/2008 |
| EP | 2882377 B1 | 11/2016 |
| EP | 3251621 | 12/2017 |
| FR | 2846545 | 5/2004 |
| FR | 2913876 | 9/2008 |
| FR | 3024835 | 2/2016 |
| FR | 3041245 | 3/2017 |
| RU | 2257174 | 7/2005 |
| RU | 2009106735 | 9/2010 |
| RU | 2694467 | 7/2019 |
| WO | WO 2011/116078 | 9/2011 |
| WO | WO 2014/117107 | 7/2014 |
| WO | WO 2015/017264 | 2/2015 |
| WO | WO 2016/044053 | 3/2016 |
| WO | WO 2017/158289 | 9/2017 |
| WO | WO 2017/164876 | 9/2017 |
| WO | WO 2017/192632 | 11/2017 |
| WO | WO 2018/152529 | 8/2018 |
| WO | WO 2018/165676 | 9/2018 |
| WO | WO 2019/073149 | 4/2019 |
| WO | WO 2019/136464 | 7/2019 |
| WO | WO 2019/169319 | 9/2019 |
| WO | WO 2021/231329 | 11/2021 |

OTHER PUBLICATIONS

Digifuse, Integra Life Sciences Corporation, USA, published Sep. 22, 2015 in 3 pages.

DuaFit In2Bones system, LMT Surgical, USA, in 4 pages, believed to be available to the public prior to May 11, 2020.

ExtremiFuse Hammertoe Fixation System, OsteoMed in 2 pages, believed to be available to the public prior to May 11, 2020.

HammerFUZE, Vilex In Tennessee, Inc, USA, in 5 pages, believed to be available to the public prior to May 11, 2020.

Hammertech Titanium,Fusion Orthopedics, USA, published in 16 pages, believed to be available to the public prior to May 11, 2020.

HammerTube™, Hammertoe System, Paragon 28, USA in 8 pages, believed to be available to the public prior to May 11, 2020.

Nextra® Hammertoe Correction System, Zimmer Biomet, USA in 10 pages, believed to be available to the public prior to May 11, 2020.

Opti-Toe®, GraMedica, USA, in 3 pages, believed to be available to the public prior to May 11, 2020.

Phalinx™ Hammertoe Fixation & Gravity™ Plantar Plate Repair, Wright Medical Group N.V., USA, in 3 pages, believed to be available to the public prior to May 11, 2020.

Preserve™ HammerGraft™ System, Surgical Technique Guide, Paragon 28 in 12 pages, believed to be available to the public prior to May 11, 2020.

Preserve™ HammerGraft™ System Paragon 28 in 2 pages, believed to be available to the public prior to May 11, 2020.

Toegrip®, Synchro Medical, France in 9 pages, believed to be available to the public prior to May 11, 2020.

ToeTac Xpress, Hammertoe fixation system, Stryker, USA in 5 pages, believed to be available to the public prior to May 11, 2020.

(56) References Cited

OTHER PUBLICATIONS

International Search Report and Written Opinion dated Aug. 31, 2021 in International Application No. PCT/US2021/031633 in 7 pages.

* cited by examiner

CANNULATED BONE IMPLANT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field of the Invention

The embodiments described herein are directed to bone implants which may be made of artificial materials (e.g., metal or polymers) or from human tissue (e.g., allograft bone).

Description of the Related Art

Hammertoe is a foot deformity that occurs in the middle joint (i.e., the proximal interphalangeal ("PIP") joint) and/or the most proximal joint (i.e., the metatarsophalangeal ("MTP") joint) of the second, third, fourth, or fifth toes. For example, FIG. 1 illustrates a diagram of the bones in a human foot 1. Hammertoe occurs in the PIP joint 6 and or the MTP joint 7 of the second, third, fourth, or fifth toes 2, 3, 4, 5. FIG. 2A illustrates a normal human foot and FIG. 2B illustrates a human foot with a hammertoe.

This condition normally starts out as a mild deformity with the hammertoes being flexible, and the symptoms can often be managed with noninvasive procedures. However, if the condition is left untreated, hammertoes will become more rigid and surgical procedures may be required to improve symptoms. This deformity can be caused by a variety of factors including: wearing certain shoes, trauma, or an abnormal balance of the toe muscles. There are approximately 200,000 cases of hammertoe in the US annually and, according to the 2012 National Foot Health Assessment commissioned by the Institute of Preventive Foot Health, 3% of U.S. adults age 21 and older, roughly 7 million people, have experienced hammertoe. Several symptoms of hammertoe include: pain in the affected toe, corns and/or callouses on the affected toe, swelling, redness, a burning sensation, inability to straighten the toe, and open sores on the affected toe.

Currently, one kind of surgery for treating hammertoe requires the use of a Kirschner wire, also known as a "K-wire," and an implant. The surgery generally involves exposing the PIP joint, removing parts of the PIP joint, pinning a K-wire centrally on the proximal phalanx, and placing in an implant.

SUMMARY

In some aspects of the disclosure, a cannulated bone implant is disclosed. The cannulated bone implant may comprise a proximal portion, a proximal end, a distal portion, a distal end, a transition portion, a threaded portion, a finned portion, and a central passage. The transition portion may be positioned between the proximal portion and the distal portion. The transition portion may comprise a bend. The threaded portion may be positioned along the proximal portion between the proximal end and the transition portion. The threaded portion may be configured to secure the implant into a bone of a patient. The finned portion may be positioned along the distal portion between the transition portion and the distal end. The finned portion may be configured to prevent migration and/or rotation of the implant in use. The central passage may extend linearly from the proximal end of the implant to the distal end of the implant.

The cannulated bone implant of the preceding paragraph can also include one or more of the following features. The threaded portion can be configured to be threaded into a proximal phalanx of the patient. The central passage can be configured to receive a surgical wire. The threaded portion can comprise a first cross-sectional shape. The finned portion can comprise a second cross-sectional shape. The first cross-sectional shape can comprise a first circle. The second cross-sectional shape can comprise a second circle or an oval. The bend can comprise an angle of 15 degrees or less. The implant can comprise a metallic material, a polymeric material, or an allograft material. The angle of the central passage can be 10 degrees or less relative to a longitudinal axis of the proximal portion. The diameter of the central passage can be constant. A height of the threads in the threaded portion can be greatest at the proximal end of the implant and gradually decrease toward the transition portion. The proximal portion can comprise a shaft. The shaft can have an outermost diameter that decreases from the transition portion toward the proximal end of the implant. The external diameter of threads of the threaded portion can be constant. The external diameter of threads of the threaded portion can be smallest at the proximal end of the implant and gradually increase from the proximal end of the implant toward the transition portion.

DETAILED DESCRIPTION

Reference will now be made in detail to various embodiments of the present technology, which relates to a bone implant. Although certain specific embodiments of the present technology are described, the present technology is not limited to these embodiments. On the contrary, these described embodiments are merely illustrative of the present technology, and the present technology is intended to also cover alternatives, modifications, and equivalents. Furthermore, in the following detailed description, numerous specific details are set forth in order to provide a thorough understanding of the present technology. However, it will be recognized by one of ordinary skill in the art that embodiments can be practiced without these specific details. In some instances, well known methods, procedures, compounds, compositions and mechanisms have not been described in detail as not to unnecessarily obscure aspects of embodiments of the present technology.

Cannulated Implant

Figure 1:
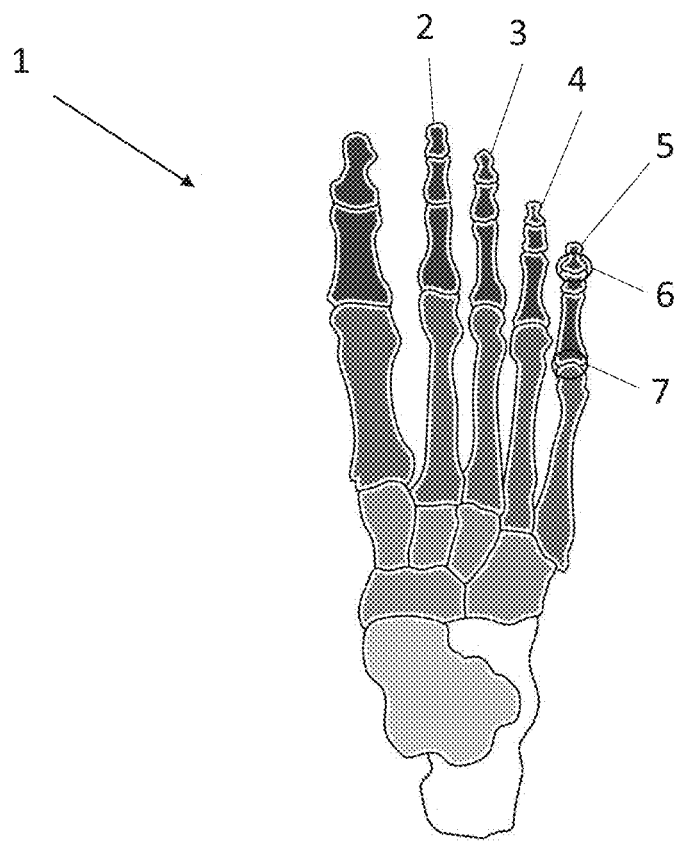
FIG. 1 illustrates a diagram of the bones of a human foot.
Figure 2A:
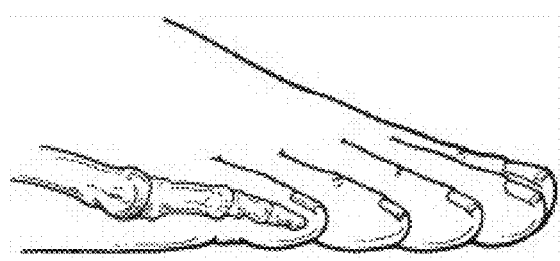
FIGS. 2A-2B illustrate a healthy human foot and a human foot with a hammertoe, respectively.
Figure 2B:
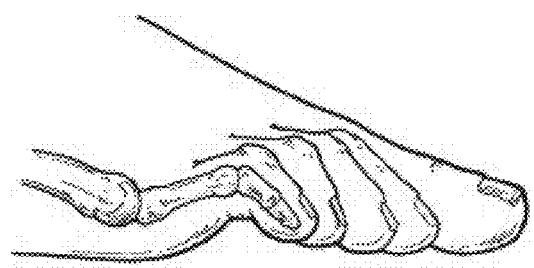
Figure 3A:
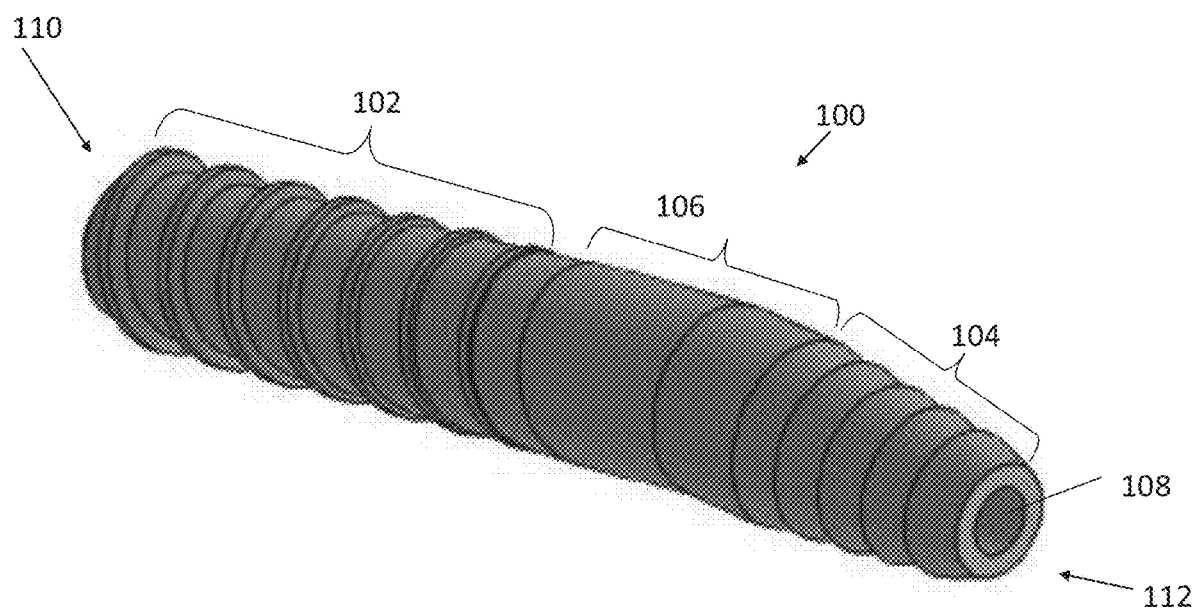
FIG. 3A illustrates a perspective view of a configuration of an implant that may be used in a hammertoe procedure.
Figure 3B:
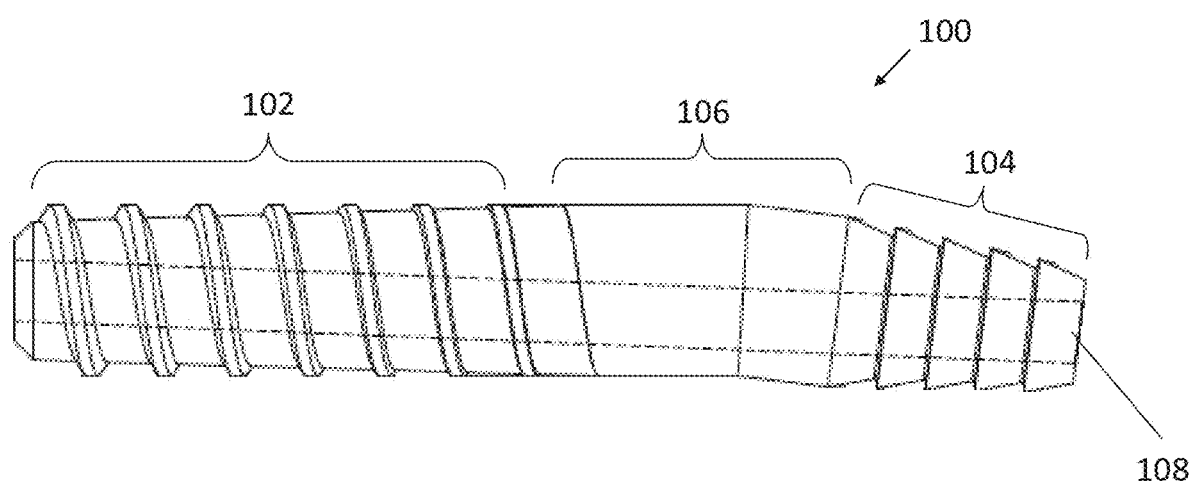
FIG. 3B illustrates a side view of the configuration of the implant shown in FIG. 3A.

FIGS. 3A-3B illustrate a configuration of an implant 100 that may be used in a hammertoe procedure. The implant 100 can have a proximal portion 102, a transition portion 106, and a distal portion 104. The transition portion 106 can be located between the proximal portion 102 and the distal portion 104. The transition portion 106 can include a bend to cause the distal portion 104 to be angled 7° relative to the proximal portion 102. In some aspects, the angle of the bend can be approximately 0° to approximately 15°, approximately 2° to approximately 13°, approximately 4° to approximately 11°, or approximately 6° to approximately 9°. In one configuration, the proximal portion 102 can be threaded and the distal portion 104 can be finned. The threaded proximal portion 102 can be configured to secure the implant 100 into a patient's bone. For example, during a hammertoe correction procedure, the threaded proximal portion 102 can be threaded into the proximal phalanx of a patient's toe. The finned distal portion 104 can be tapered with a larger diameter at the distal end of the transition portion 106 and a smaller diameter at the distal end 112 of the implant 100. A tapered finned distal portion 104 prevents the implant 100 from migrating after the implant 100 has been inserted into a patient while promoting micro-motion and bone healing. In a configuration, the shaft of the implant 100 forming the proximal portion 102 can have a diameter that is smallest at a proximal end 110 and gradually increases to a maximum diameter in the transition portion 106.

As shown in FIG. 3B, the implant 100 can be cannulated with a straight, narrow passage 108 therein, extending linearly from the proximal end 110 to the distal end 112 of the implant 100, as shown below. The angle of the passage 108 can be approximately 4.5° relative to a longitudinal axis of the proximal portion 102. In some aspects, the angle of the passage 108 can be approximately 0° to approximately 10°, approximately 2° to approximately 8°, or approximately 4° to approximately 6° relative to a longitudinal axis of the proximal portion 102. The implant 100 can be made out of allograft, metal, or polymer.

Figure 4A:
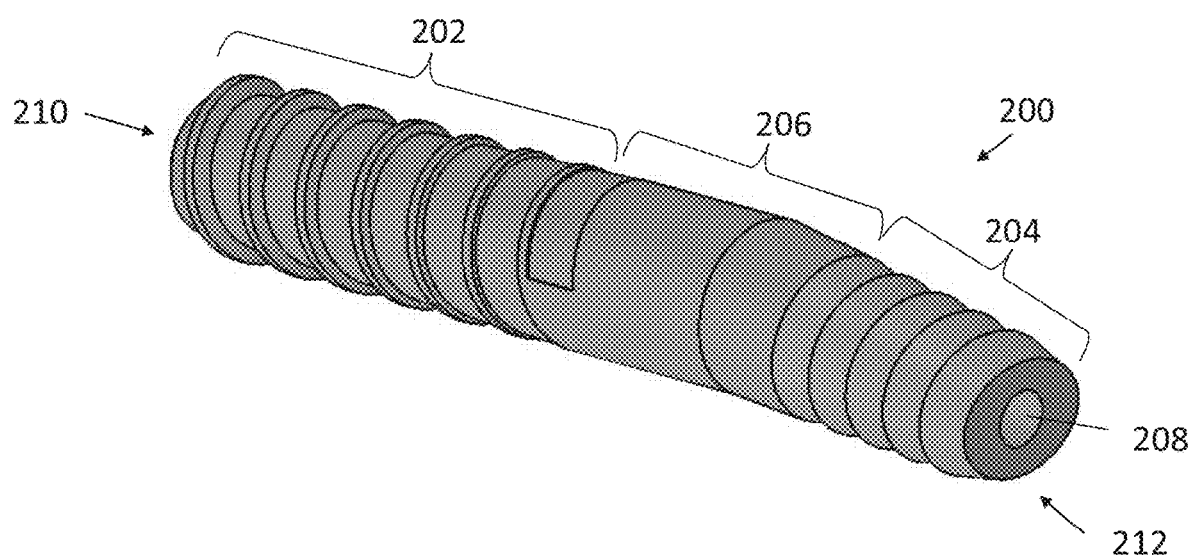
FIG. 4A illustrates a perspective view of a configuration of an implant that may be used in a hammertoe procedure.
Figure 4B:
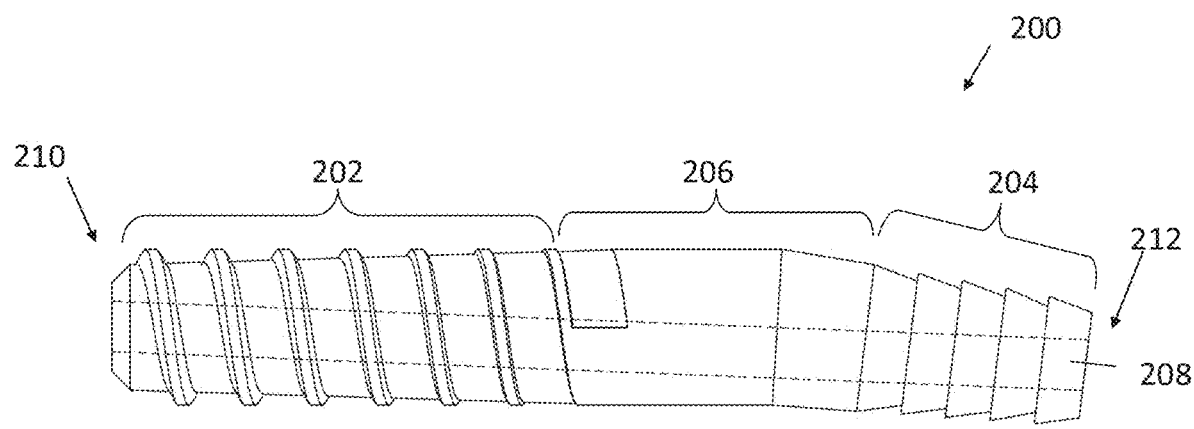
FIG. 4B illustrates a side view of the configuration of the implant shown in FIG. 4A.

FIGS. 4A-4B illustrate another configuration of an implant 200 that can be used in a hammertoe procedure. Features of the implant 200 may also be incorporated into the implant 100, and vice versa. The implant 200 can have a proximal portion 202, a transition portion 206, and a distal portion 204. The transition portion 206 can be located between the proximal portion 202 and the distal portion 204. The transition portion 206 can include a bend to cause the distal portion 204 to be angled 7° relative to the proximal portion 202. In some aspects, the angle of the bend can be approximately 0° to approximately 15°, approximately 2° to approximately 13°, approximately 4° to approximately 11°, or approximately 6° to approximately 9°. In one embodiment, the proximal portion 202 can be threaded and the distal portion 204 can be finned. The threaded proximal portion 202 can be configured to secure the implant 200 into a patient's bone. For example, during a hammertoe correction procedure, the threaded proximal portion 202 can be threaded into the proximal phalanx of a patient's toe. The finned distal portion 204 can be tapered with a larger diameter at the distal end of the transition portion 206 and a smaller diameter at the distal end 212 of the implant 200.

In an embodiment, the shaft of the implant 200 forming the proximal portion 202 can have a diameter that is smallest at a proximal end 210 and gradually increases to a maximum diameter in the transition portion 206. The threads on the proximal portion 202 can be reverse tapered or graduated relative to the taper of the shaft of the implant 200. For example, the threads on the proximal portion 202 can have a height relative to the shaft of the implant 200 that is greater at a proximal end 210 and that decreases toward the transition portion 206. The external diameter of the threads along the proximal portion 202 may be constant from the proximal end 210 toward the transition portion 206. This configuration ensures effective contact between the implant 200 and the surgical site. The negative space between the threads allows for new bone to incorporate into the implant 200, which is important for patients who have poor quality bones. In some embodiments, the external diameter of the threads along the proximal portion 202 may gradually increase from the proximal end 210 toward the transition portion 206.

As shown in FIG. 4B, the implant 200 can also be cannulated with a straight, narrow passage 208 therein, extending linearly from the proximal end 210 to the distal end 212 of the implant 200, as shown below. The angle of the passage 208 can be approximately 4.5° relative to a longitudinal axis of the proximal portion 202. In some aspects, the angle of the passage 108 can be approximately 0° to approximately 10°, approximately 2° to approximately 8°, or approximately 4° to approximately 6° relative to a longitudinal axis of the proximal portion 202. The implant 200 can be made out of allograft, metal, or polymer.

Figure 5A:
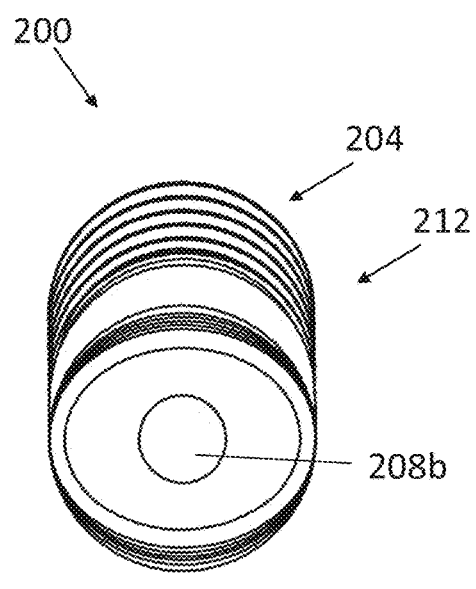
FIG. 5A illustrates a distal end of the implant shown in FIG. 4A.
Figure 5B:
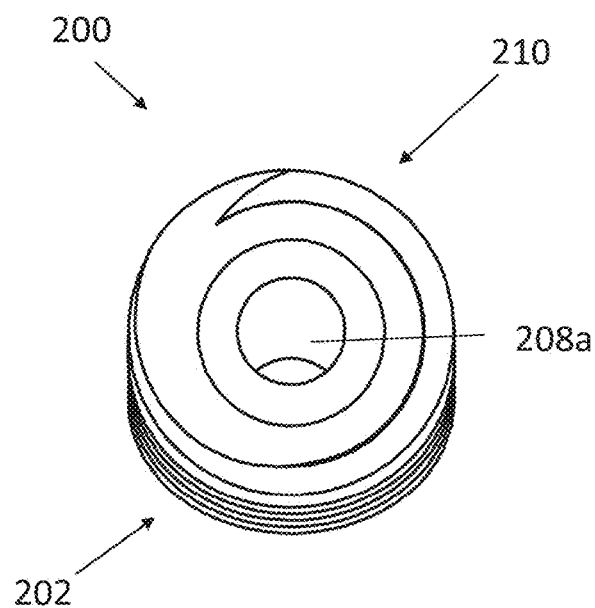
FIG. 5B illustrates a proximal end of the implant shown in FIG. 4A.

As shown in FIGS. 5A-5B, the distal portion 204 can have a cross-sectional shape that is generally oblong or oval while the proximal portion 202 can have a cross-sectional shape that is generally circular. A serrated or finned distal portion 204 that is tapered and has a generally oblong cross-sectional shape prevents the implant 200 from migrating or rotating after the implant 200 has been inserted into a patient. This configuration also promotes micro-motion and bone healing.

The openings 208a, 208b of passage 208 may comprise a generally circular shape that extends through the implant 200. In some embodiments, the passage 208 extending from the opening 208a at the proximal end 210 through the proximal portion 202 may have a different diameter than the passage 208 extending from the opening 208b at the distal end 212 through the distal portion. For example, the diameter of the passage 208 may be greater at the distal portion 204 than the diameter of the passage 208 at the proximal portion 202. In some embodiments, the passage 208 has a constant diameter throughout the implant 200.

Method of Use

The implants 100, 200 described above can be used in a hammertoe correction procedure. In one method of performing the procedure, a practitioner makes a longitudinal incision along the affected digit, such as along the top (dorsal side) of the foot across a middle phalanx, the PIP joint and a proximal phalanx. Next, the practitioner performs a transverse capsular and tendon incision, such that the PIP joint is exposed. A sagittal saw or reamer can be used to resect the articular cartilage at the base of the middle phalanx and bone and cartilage at the head of the proximal phalanx to allow for reduction of the digit. A K-wire can be used to pre-drill or otherwise prepare the center of the proximal and middle phalanges, if desired or necessary. The practitioner may insert an instrument (e.g., a drill, a tap, or combination of a drill and a tap) into the proximal phalanx until the instrument reaches a certain depth within the proximal phalanx. The instrument may comprise a threaded portion configured to match the threaded portions 102, 202 of the implant 100, 200. The instrument may have one or more markings that indicate various depths of insertion of the instrument. The instrument may have a plurality of markings that indicate a depth of 1 mm, 2 mm, 3 mm, 4 mm, 5 mm, 6 mm, 7 mm, 8 mm, or more. For example, when the 4 mm marking of the instrument aligns with the distal surface of the proximal phalanx, the instrument is inserted 4 mm into the proximal phalanx. A proximal screw-in ream or tap and/or a distal reaming may be performed over the K-wire. Compared with using a saw, the distal reaming could spare more bone and/or tissue to allow for better integration of the implant 100, 200.

After the proximal and middle phalanges are appropriately prepared, the implant 100, 200 as described above can be delivered. Preferably with the K-wire removed from the digit, the implant 100, 200 may first be delivered into the proximal phalanx to an appropriate depth. For example, the proximal, threaded portion 102, 202 of the implant 100, 200 may be threaded into the proximal phalanx using an appropriate insertion device.

Next, with the distal portion 104, 204 of the implant 100, 200 extending from the proximal phalanx, the distal portion of the toe (i.e., the middle and distal phalanges) can be distracted distally to advance the distal portion 104, 204 of the implant 100, 200 into the middle phalanx. In some embodiments of the method, the distal portion 104, 204 of the implant 100, 200 is placed over a K-wire and manually compressed. The K-wire can be initially passed through the proximal portion of the middle phalanx until the K-wire extends past the distal end of the distal phalanx. As described above, a proximal screw-in ream or tap and a distal reaming may be performed over the K-wire. The middle phalanx can then be pushed onto the distal portion 104, 204 of the implant 100, 200 and secured via a press fit. The K-wire is then advanced into the proximal portion 102, 202 of the implant 100, 200 and the proximal phalanx. Optionally, the K-wire can cross the MTP joint. Finally, the soft tissue and incisions are closed.

Other Variations and Terminology

The terms "first" and "second" are merely numbered for describing corresponding technical features clearly and do not represent the actual order. During particular implementations, the locations of the technical features defined by the terms "first" and "second" are interchangeable.

Terms of orientation used herein, such as "top," "bottom," "horizontal," "vertical," "longitudinal," "lateral," "outer," "inner," and "end" are used in the context of the illustrated embodiment. However, the present disclosure should not be limited to the illustrated orientation. Indeed, other orientations are possible and are within the scope of this disclosure. Terms relating to circular shapes as used herein, such as "diameter" or "radius," should be understood not to require perfect circular structures, but rather should be applied to any suitable structure with a cross-sectional region that can be measured from side-to-side. Terms relating to shapes generally, such as "circular" or "cylindrical," "semi-circular" or "semi cylindrical," "oval" or "oblong," or any related or similar terms, are not required to conform strictly to the mathematical definitions of circles, cylinders, oblongs, ovals or other structures, but can encompass structures that are reasonably close approximations.

The terms "approximately," "about," and "substantially" as used herein represent an amount close to the stated amount that still performs a desired function or achieves a desired result. For example, in some embodiments, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Conditional language, such as "can," "could," "might," or "may," unless specifically stated otherwise or otherwise understood within the context as used, is generally intended to convey that certain embodiments include or do not include, certain features, elements and/or steps. Thus, such conditional language is not generally intended to imply that features, elements and/or steps are in any way required for one or more embodiments.

Conjunctive language, such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require the presence of at least one of X, at least one of Y and at least one of Z.

Some embodiments have been described in connection with the accompanying drawings. The figures are drawn to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed and/or rearranged. Further, the disclosure herein of any particular feature, aspect, method, property, characteristic, quality, attribute, element or the like in connection with various embodiments can be used in all other embodiments set forth herein. Additionally, any methods described herein may be practiced using any device suitable for performing the recited steps.

Although this invention has been disclosed in the context of certain embodiments and examples, the scope of this disclosure extends beyond the specifically disclosed embodiments to other alternative embodiments and/or uses of the invention and obvious modifications and equivalents thereof. Any system, method, and device described in this application can include any combination of the preceding features described in this and other paragraphs, among other features and combinations described herein, including features and combinations described in subsequent paragraphs. While several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Various features and aspects of the disclosed embodiments can be combined with or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A cannulated bone implant, comprising:
    a proximal portion, a proximal end, a distal portion, and a distal end;
    an angled transition portion positioned between the proximal portion and the distal portion;

a threaded portion positioned along the proximal portion between the proximal end and the transition portion, wherein the threaded portion is configured to secure the implant into a bone of a patient;

a finned portion positioned along the distal portion between the transition portion and the distal end, wherein the finned portion is configured to prevent migration and/or rotation of the implant in use; and a central passage extending linearly from the proximal end of the implant, through the angled transition portion and to the distal end of the implant, wherein the central passage is at a non-zero angle relative to the proximal portion and the distal portion of the implant.

2. The cannulated bone implant of claim 1, wherein the threaded portion is configured to be threaded into a proximal phalanx of the patient.

3. The cannulated bone implant of claim 1, wherein the central passage is configured to receive a surgical wire.

4. The cannulated bone implant of claim 1, wherein the threaded portion comprises a first cross-sectional shape and the finned portion comprises a second cross-sectional shape.

5. The cannulated bone implant of claim 4, wherein the first cross-sectional shape comprises a first circle.

6. The cannulated bone implant of claim 4, wherein the second cross-sectional shape comprises a second circle.

7. The cannulated bone implant of claim 4, wherein the second cross-sectional shape comprises an oval.

8. The cannulated bone implant of claim 1, wherein the angled transition portion comprises an angle of 15 degrees or less.

9. The cannulated bone implant of claim 1, wherein the implant comprises a metallic material.

10. The cannulated bone implant of claim 1, wherein the implant comprises a polymeric material.

11. The cannulated bone implant of claim 1, wherein the implant comprises an allograft material.

12. The cannulated bone implant of claim 1, wherein an angle of the central passage is 10 degrees or less relative to a longitudinal axis of the proximal portion.

13. The cannulated bone implant of claim 1, wherein a diameter of the central passage is constant.

14. The cannulated bone implant of claim 1, wherein a height of threads in the threaded portion is greatest at the proximal end of the implant and gradually decreases toward the angled transition portion.

15. The cannulated bone implant of claim 1, wherein the proximal portion comprises a shaft having an outermost diameter that decreases from the angled transition portion toward the proximal end of the implant.

16. The cannulated bone implant of claim 1, wherein an external diameter of threads of the threaded portion is constant.

17. The cannulated bone implant of claim 1, wherein an external diameter of threads of the threaded portion is smallest at the proximal end of the implant and gradually increases from the proximal end of the implant toward the transition portion.

18. A cannulated bone implant, comprising:

a proximal portion, a proximal end, a distal portion, and a distal end;

an angled transition portion positioned between the proximal portion and the distal portion;

a helically threaded portion positioned along the proximal portion between the proximal end and the transition portion, wherein the helically threaded portion is configured to secure the implant into a proximal phalanx of a patient;

a finned portion comprising a plurality of parallel fins positioned along the distal portion between the transition portion and the distal end, wherein the finned portion is configured to be inserted into a middle phalanx of the patient and to prevent migration and/or rotation of the implant in use, wherein the finned portion is shorter in length than the threaded portion; and a central passage extending linearly from the proximal end of the implant, through the angled transition portion and to the distal end of the implant;

wherein an angle of the central passage is 10 degrees or less relative to a longitudinal axis of the proximal portion.

19. The cannulated bone implant of claim 18, wherein the helically threaded portion comprises a first cross-sectional shape and the finned portion comprises a second cross-sectional shape, wherein the first cross-sectional shape comprises a first circle and the second cross-sectional shape comprises an oval.

20. The cannulated bone implant of claim 18, wherein the finned portion is tapered with a larger diameter at a distal end of the transition portion and a smaller diameter at the distal end of the implant.

* * * * *